United States Patent
Schorn et al.

(10) Patent No.: US 10,428,089 B2
(45) Date of Patent: Oct. 1, 2019

(54) METHOD FOR PRODUCING TRIALKYLGALLIUM COMPOUNDS AND THE USE THEREOF

(71) Applicant: Umicore AG & Co. KG, Hanau-Wolfgang (DE)

(72) Inventors: Wolf Schorn, Giessen (DE); Jörg Sundermeyer, Marburg (DE); Annika Frey, Hanau (DE); Ralf Karch, Kleinostheim (DE); Andreas Rivas-Nass, Bensheim (DE); Eileen Woerner, Nidderau (DE); Angelino Doppiu, Seligenstadt (DE)

(73) Assignee: Umicore AG & Co. KG (DE)

( * ) Notice: Subject to any disclaimer, the term of this patent is extended or adjusted under 35 U.S.C. 154(b) by 37 days.

(21) Appl. No.: 15/126,043

(22) PCT Filed: Mar. 12, 2015

(86) PCT No.: PCT/EP2015/055211
§ 371 (c)(1),
(2) Date: Sep. 14, 2016

(87) PCT Pub. No.: WO2015/136049
PCT Pub. Date: Sep. 17, 2015

(65) Prior Publication Data
US 2017/0081344 A1  Mar. 23, 2017

(30) Foreign Application Priority Data

Mar. 14, 2014  (EP) .................................... 14159973

(51) Int. Cl.
*C07F 5/00* (2006.01)
*H01L 21/02* (2006.01)
*C23C 16/18* (2006.01)

(52) U.S. Cl.
CPC ............... *C07F 5/00* (2013.01); *C23C 16/18* (2013.01); *H01L 21/0262* (2013.01)

(58) Field of Classification Search
USPC ............................................ 556/1, 170, 186
See application file for complete search history.

(56) References Cited

U.S. PATENT DOCUMENTS

| | | | | |
|---|---|---|---|---|
| 5,043,462 A | * | 8/1991 | Sundermeyer | C07F 5/00 556/1 |
| 5,663,390 A | | 9/1997 | Giolando | |
| 5,817,847 A | * | 10/1998 | Giolando | C07F 5/00 556/1 |
| 9,108,985 B2 | * | 8/2015 | Karch | C23C 16/301 |
| 2004/0260106 A1 | * | 12/2004 | Honma | C07F 5/00 556/1 |

FOREIGN PATENT DOCUMENTS

| | | |
|---|---|---|
| EP | 0399190 A1 | 11/1990 |
| JP | H02295991 A | 12/1990 |
| JP | H11514677 A | 12/1999 |
| WO | WO-2012150229 A1 | 11/2012 |
| WO | WO-2013083450 A1 | 6/2013 |
| WO | WO-2014093419 A1 | 6/2014 |

OTHER PUBLICATIONS

International Search Report for PCT/EP2015/055211 dated Jun. 23, 2015.
Beachley, O.T., "Monomoeric Organogallium-Nitrogen Compounds, Chemistry of $Et_2GaNH[C_6H_2(2,4,6\text{-}t\text{-}Bu)_3]$ with Decomposition to the Metallacycle", Organometallics, 1999, vol. 18, No. 13, pp. 2543-2549.
Beachley, O.T., et al., "Synthesis and Characterization of Monomeric Organogallium-Nitrogen Componds, $Et_2GaNMe[C_6H_2(2,4,6\text{-}t\text{-}Bu)_3]$, $Me_2GaNMe[C_6H_2(2,4,6\text{-}t\text{-}Bu)_3]$, $MeGa\{NH[C_6H_2(2,4,6\text{-}t\text{-}Bu)_3]\}_2$, and $Ga\{NH[C_6H_2(2,4,6\text{-}t\text{-}Bu)_3]\}_3$", Organometallics, 2001, vol. 20, pp. 945-949.
Gynane, M., et al., "Formation of methyl-and ethylgallium halides by te direct reaction between the metal and alkyl halide", Journal of Organometallic Chemistry, 1972, vol. 40, pp. C59-C60.
Jegier, J, et al., "Bis(dimethylamido) Complexes of Alkyl- and Phenyigallium. Useful Precursors to the $RGa^{2+}$ Synthon", Inorganic Chemisry, 2001, vol. 40, No. 23, pp. 6017-6021.
Krause, H., et al., "Methylmetall-bis(trimethylsiyl)amidoderivatives des Alumniniums, Galliums und Arsens", Zeitschrift für anorganische und allgemeine Chemie, 1988, vol. 563, No. 1, pp. 116-126.
Linti, G., et al., "Darstellung und Strukturen monomerer (2,2,6,6-Tetramethylpiperidino)gallane", Chemische Berichte, 1994, vol. 127, No. 8, pp. 1387-1393.
Macdonald, C., et al., "Group 13 decamethylmetallocenium cations", Dalton Transactions, 2008, No. 9, pp. 1161-1176.
Schmidbaur, H., et al., "Neue Wege zu Organogalliumhalogeniden", Chemische Berichte Jahrg, 1966, vol. 99, pp. 2187-2196.

* cited by examiner

*Primary Examiner* — Pancham Bakshi
(74) *Attorney, Agent, or Firm* — Drinker Biddle & Reath LLP

(57) ABSTRACT

The invention relates to an improved process for inexpensive and environmentally benign preparation of trialkylgallium compounds of the general formula:

$R_3Ga$ in high yield and selectivity, where R is alkyl of 1 to 4 carbon atoms. Trialkylgallium is prepared according to the invention via the intermediate stage alkylgallium dichloride ($RGaCl_2$) or dialkylgallium chloride/alkylgallium dichloride mixture ($R_2GaCl/RGaCl_2$). The $RGaCl_2$ obtained or the $R_2GaCl/RGaCl_2$ mixture also forms part of the subject-matter of the present invention.
The novel process of the present invention is notable for improved process management. The process intentionally makes substantial use of inexpensive starting materials and reagents of low environmental impact and so is also useful for the industrial scale.
The trialkylgallium compounds obtained are very pure and so are particularly useful as organometallic precursor for metal-organic chemical vapor deposition (MOCVD) or metal-organic vapor phase epitaxy (MOVPE) in semiconductor and microsystem technology.

21 Claims, No Drawings

METHOD FOR PRODUCING TRIALKYLGALLIUM COMPOUNDS AND THE USE THEREOF

CROSS-REFERENCE TO RELATED APPLICATIONS

This application is a national stage application (under 35 U.S.C. § 371) of PCT/EP2015/055211, filed Mar. 12, 2015, which claims benefit of European Application No. 14159973.8, filed Mar. 14, 2014, both of which are incorporated herein by reference in their entirety.

The invention relates to a process for preparing trialkylgallium compounds. This process involves the preparation of alkylgallium dichloride, or of a dialkylgallium chloride/alkylgallium dichloride mixture, whence trialkylgallium compounds are subsequently obtainable.

Trialkylgallium compounds are used in particular as organometallic precursors for metal-organic chemical vapour deposition (MOCVD) or metal-organic vapour phase epitaxy (MOVPE).

PRIOR ART

The prior art describes various processes for preparing precursors for MOCVD and/or MOVPE processes. These processes are used in particular in the manufacture of films for optoelectronic applications such as solar cells or LEDs, which typically requires very high purity of the particular organometallic precursor used and the absence or only very minimal presence of oxygen-containing impurities.

Thus, various processes for preparing trialkylindium, trialkylgallium or else trialkylaluminium compounds are known. However, process conditions in any one case do not necessarily transfer without changes. It must be borne in mind that the elements aluminium, gallium and indium as such have unalike chemical behaviours, which generally means that the preparation of trialkylindium, trialkylgallium or trialkylaluminium compounds requires a special, dedicated process in each case.

Prior art processes for preparing trialkylgallium compounds often have appreciable difficulties to produce the trialkylgallium compounds, specifically trimethylgallium, in the amount and purity required for customary uses. To wit, impurities in the precursors may have an appreciable adverse effect on the electrical properties of semiconductor layers produced from the precursors via MOCVD or MOVPE. Many processes are additionally very time-consuming.

Moreover, they frequently only give low yields and the reaction steps are frequently characterized by reduced selectivity. The use of large amounts of organic solvents is another reason why existing processes are usually costly, not very environmentally friendly and entail solvent residues in the intermediate and end products, which in turn may restrict the use of the end products to an appreciable degree or necessitate costly and inconvenient purification. Furthermore, iodine or bromine is in some instances used as an activator in the preparation of alkylgallium compounds, which likewise entails impurities which may put appreciable limits on later use. Individual processes, what is more, envisage the introduction of $H_2$, further amplifying their cost and inconvenience.

WO 2013/083450 A1 relates to a process for preparing trialkylgallium from gallium trichloride and an alkylaluminium compound. However, gallium trichloride is a very expensive reactant, hygroscopic and corrosive, making it necessary to adopt costly and inconvenient measures which make such a process very costly overall.

U.S. Pat. No. 5,663,390 relates to a process for preparing organo metal chlorides from elemental metal. Gallium is one metal used. An essential part of the process is the addition of $H_2$ to sufficiently activate the reaction making the overall process costly and inconvenient. No yield is reported for the recited reaction product $R_2GaCl$, nor its purity. In addition, high temperatures of about 240° C. are envisaged for the reaction, so the process does not have convenient apparatus requirements.

WO 2012/150229 A1 describes a process for preparing trialkylgallium wherein gallium is reacted with alkyl chloride in the presence of a Lewis acid catalyst. The reaction product is stated to be alkylgallium sesquichloride ($R_3Ga_2Cl_3$). The Lewis acid is formed especially in situ, for which especially iodine or bromine is added to the reaction mixture. The latter leads to unacceptable impurities in the reaction product which are, in particular, very difficult to remove. The $R_3Ga_2Cl_3$ obtained is not isolated, being converted into trialkylgallium directly without further characterization. The overall reaction is not atom-economical.

Gynane and Worrall describe the reaction of gallium with an alkyl bromide or alkyl iodide to form alkylgallium sesquihalides or a mixture of alkylgallium dihalides and dialkylgallium halides (M. J. S. Gynane, I. J. Worrall, J. Organomet. Chem, 1972, 40, C59). The reaction takes place at room temperature and requires reaction times of at least two up to four weeks. The process conditions described do not transfer to the reaction of gallium with alkyl chlorides. Yields are not reported nor the purity of the reaction products obtained.

A method of preparing alkylgallium compounds has further been described by Schmidbaur and Findeiss. Methylgallium dichloride is prepared therein from $GaCl_3$ and $Me_4Si$ or $GaCl_3$ and $(Me_3Si)_2O$ (H. Schmidbaur, W. Findeiss, Chem. Ber. 1966, 99, 2187). However, this preparation is likewise costly because of the starting materials and therefore not very suitable for the industrial scale.

OBJECT

It is an object of the present invention to provide a process for preparing trialkylgallium compounds in an inexpensive as well as simple and fast manner. The process shall also provide trialkylgallium compounds in high yield and high purity. More particularly, the trialkylgallium compounds shall ideally be free of oxygen impurities.

As a result, the trialkylgallium compounds obtained shall be particularly useful as organometallic precursors for metal-organic chemical vapour deposition (MOCVD) or metal-organic vapour phase epitaxy (MOVPE), which each require high-purity organo metal compounds for the production of semiconductor layers.

The process shall further be performable with a low level of environmental impact and with a low level of resource intensity.

Solution

The object of the present invention is achieved by the subjects of the claims. The object is achieved in particular by an improved process for preparing trialkylgallium compounds of the general formula:

$R_3Ga$, where R is alkyl of 1 to 4 carbon atoms. Said alkyl may be branched or unbranched, preferably unbranched. The process of the present invention is particularly useful for preparing triethylgallium and trimethylgallium and very particularly useful for preparing trimethylgallium. R is thus preferably selected from ethyl and methyl and most preferably is methyl, also abbreviated to Me hereinbelow.

SUMMARY OF THE INVENTION

1. Process for preparing a compound (A), which is either of the general formula:

$RGaCl_2$ or is a mixture of $R_2GaCl$ with $RGaCl_2$, comprising the reaction steps of
    a1) reacting gallium with an alkyl donor in the presence of an activator to form compound (A), wherein the alkyl donor is an alkyl chloride, and the activator is a gallium component.
    a2) and optionally isolating said compound (A) from the reaction mixture,
    where R is branched or unbranched alkyl of 1 to 4 carbon atoms and wherein preferably the ratio of $R_2GaCl$ to $RGaCl_2$ is in the range from 10:90 to 90:10, in particular from 10:90 to 50:50, in particular from 20:80 to 40:60, based on the molar amounts.
2. Process according to Point 1, wherein the alkyl donor has the general formula:

RCl where R is as defined above, and wherein the alkyl donor is preferably in gaseous form.
3. Process according to Point 1 or 2, wherein the activator is a compound or mixture of compounds having the following general formula:

$R_aGa_bCl_c$, where a is selected from 0, 1, 2 and 3, b is selected from 1 and 2, and c is selected from 0, 1, 2 and 3 subject to the proviso that a and c are not both 0 and a+b+c is =4 or a multiple of 4, and where R is as defined above and where the sum total of a and c is 3 when b is 1, or where the sum total of a and c is 6 when b is 2.
4. Process according to any preceding point, wherein the activator is selected from $GaCl_3$, $R_2GaCl$, $R_3Ga_2Cl_3$, $RGaCl_2$ and mixtures thereof, or preferably wherein the reaction product, compound (A), is itself used as activator.
5. Process according to any preceding point, wherein the activator is selected from $RGaCl_2$, $GaCl_3$, $R_3Ga_2Cl_3$ and mixtures thereof.
6. Process according to any preceding point, wherein R is methyl or ethyl, preferably methyl.
7. Process according to any preceding point, wherein the molar ratio of alkyl donor to gallium is at least 1.4:1.
8. Process according to at least one of the preceding points, wherein a premix of gallium and activator is initially charged to the reaction vessel in reaction step a1) and the alkyl donor is added subsequently.
9. Process according to Point 8, wherein the reactant mixture is heated to temperatures between 120° C. and 200° C.
10. Process according to Point 9, wherein the temperatures are maintained for at least 30 min and at most 50 hours.
11. Process according to any preceding point, wherein reaction step a1) is carried out in the absence of organic solvents.
12. Process according to any preceding point, wherein step a) comprising isolating said compound (A) from the reaction mixture as reaction step a2), and wherein said step of isolating said compound (A) from the reaction mixture comprises separating unconverted reactants from the reaction mixture.
13. Process according to any preceding point, wherein the yield of compound (A) is above 90% based on gallium metal used.
14. Process according to any preceding point, wherein the purity of compound (A) is more than 99%.
15. Process for preparing a compound (B) of the general formula:

$R_3Ga$ which process comprises providing a compound (A) according to one or more of the preceding points, and
    b) reacting said compound (A) with a metal alkyl component to obtain a compound (B) of the general formula:

$R_3Ga$ where R is as defined in any preceding point.
16. Process according to Point 15, wherein the metal alkyl component has the general formula:

$R_dM_eX_f$ where d is selected from 1, 2 and 3, e is selected from 1 and 2 and f is selected from 0, 1, 2 and 3 subject to the proviso that d and f are not both 0, and where R is as defined above, and where M is selected from aluminium, lithium and magnesium, and where X is selected from Cl, Br and I.
17. Process according to Point 16, wherein M is aluminium, e is =1 or 2 and the sum total of d, e and f is =4 or 8, and wherein d is ≠0, and wherein X is Cl.
18. Process according to any of Points 15 to 16, wherein the metal alkyl component is selected from RMgCl, $R_2AlCl$, $R_3Al$, $R_3Al_2Cl_3$ and RLi,
19. Process according to any of Points 15 to 18, wherein an auxiliary base is also added in reaction step b), wherein the auxiliary base is selected from sodium chloride, potassium chloride, aluminium chloride and mixtures thereof.
20. Process according to any of Points 15 to 19, wherein the yield of compound (B) is above 90%.
21. Process according to any of Points 15 to 20, wherein the purity of compound (B) is at least 99%.
22 Use of compound (B) obtained by a process according to any of Points 15 to 21 as precursor for metal-organic chemical vapour deposition (MOCVD) or metal-organic vapour phase epitaxy (MOVPE).
23. Use of compound (A) according to Point 1 for producing compound (B) according to Point 15.
24. Compound (A) obtained by a process according to any of Points 1 to 14.
25. Compound (B) obtained by a process according to any of Points 15 to 21.

DETAILED DESCRIPTION OF THE INVENTION

The trialkylgallium compound is prepared according to present invention via the intermediate stage of compound (A), which may be alkylgallium dichloride or a dialkylgallium chloride/alkylgallium dichloride mixture:

$RGaCl_2$ or, respectively, $R_2GaCl/RGaCl_2$ where R is alkyl of 1 to 4 carbon atoms. The ratio between $R_2GaCl$ and $RGaCl_2$ is in the range from 10:90 to 90:10, in particular from 10:90 to 50:50, in particular from 20:80 to 40:60, based on the molar amounts. The alkyl moiety may be branched or unbranched, preferably unbranched. R is preferably selected from ethyl and methyl and most preferably R is methyl. The $RGaCl_2$ or $R_2GaCl/RGaCl_2$ obtainable in high yield and purity by the process of the present invention in a fast manner may subsequently be used for preparing trialkylgallium compounds of the present invention.

This in turn allows the preparation of trialkylgallium compounds from elemental gallium in high purity and high yield in a fast process.

The process intentionally makes substantial use of inexpensive starting materials and reagents of low environmental impact and so is also useful for the industrial scale. More particularly, the invention substantially eschews the use of customarily required organic solvents, which contributes to cost-effective and environmentally benign process management.

It is especially versus prior art processes proceeding from $GaCl_3$ that the process of the present invention provides for more economical and faster preparation of trialkylgallium compounds and thus is more suitable for practice on the industrial scale.

The trialkylgallium compounds obtained are of particularly high purity and so are particularly suitable for the production of gallium-containing films in the semiconductor industry and in the related electronics industry, in the context of metal-organic chemical vapour deposition (MOCVD) or metal-organic vapour phase epitaxy (MOVPE).

The process of the present invention comprises the step of:
a) preparing alkylgallium dichloride or an $R_2GaCl/RGaCl_2$ mixture.

Step a) may be followed by a further step of:
b) preparing the trialkylgallium compound from alkylgallium dichloride or $R_2GaCl/RGaCl_2$ mixture.

Step b) may follow on from step a) directly or be carried out after step a) with a time delay, i.e. when needed.

It has been found to be particularly advantageous to prepare trialkylgallium compounds via the intermediate stage of compound (A), alkylgallium dichloride ($RGaCl_2$) or $R_2GaCl/RGaCl_2$ mixture. This intermediate stage is obtainable in high purity according to the present invention. $RGaCl_2$ or $R_2GaCl/RGaCl_2$ mixture is further obtained in good yield and is simple to isolate, so trialkylgallium compound is obtainable from this intermediate stage in a rapid and controlled manner.

Moreover, particularly pure trialkylgallium compounds were obtained in high yield and a short time with such a process. The invention accordingly provides for the preparation of $RGaCl_2$ or $R_2GaCl/RGaCl_2$ mixture comprising step a), which may in turn be followed by the preparation of the trialkylgallium compound comprising step b). Usage of $RGaCl_2$ or $R_2GaCl/RGaCl_2$ mixture as an intermediate stage in the preparation of trialkylgallium compounds largely avoids the need to use customary and cost-intensive reactants for preparing trialkylgallium compounds, in particular the use of high amounts of $GaCl_3$, as is typically necessary in existing processes. Furthermore, $RGaCl_2$ or $R_2GaCl/RGaCl_2$ mixture already includes one or, respectively, more alkyl groups, so the amounts of alkylating agents typically used for preparing trialkylgallium can be greatly reduced with the process of the present invention.

a) Preparation of Alkylgallium Dichloride

The preparation of $RGaCl_2$ or $R_2GaCl/RGaCl_2$ mixture comprises the following reaction step:
a1) reacting elemental gallium with an alkyl donor in the presence of an activator to form $RGaCl_2$ or $R_2GaCl/RGaCl_2$ mixture
a2) and optionally isolating the $RGaCl_2$ or the $R_2GaCl/RGaCl_2$ mixture from the reaction mixture.

In preferred embodiments, the preparation of $RGaCl_2$ or of the $R_2GaCl/RGaCl_2$ mixture in the manner of the present invention comprises step a2), i.e. the $RGaCl_2$ or the $R_2GaCl/RGaCl_2$ mixture is isolated from the reaction mixture. The term "isolation" or "isolating" encompasses the separating of the particular desired reaction product from the mixture present in the reaction vessel by removing the reaction product from the reaction vessel, or the removing of other compounds aside from the reaction product from the reaction mixture such that the reaction product remains behind in the reaction vessel.

In alternative embodiments, step a) of the present invention does not include the reaction step a2) and so there is no isolation of compound (A), $RGaCl_2$ or $R_2GaCl/RGaCl_2$ mixture from the reaction mixture. In such embodiments, therefore, step b) may follow on from step a) without prior isolation of $RGaCl_2$ or $R_2GaCl/RGaCl_2$ mixture from the reaction mixture.

Reaction Step a1):

The alkyl donor in the present invention is any compound comprising an alkyl group in that, in the present invention, the alkyl donor is an alkyl chloride, i.e. a compound comprising at least one chlorine atom as well as the alkyl group. The alkyl donor preferably has the following general formula:

where R is as defined above. Alkyl donors of this type are available at low cost by comparison with, for example, alkyllithium compounds. R is more preferably selected from methyl and ethyl and is further preferably methyl. It is thus particularly preferable for the alkyl donor to be methyl chloride.

The molar ratio of alkyl donor to gallium is preferably at least 1.4:1, preferably at least 1.6:1 and more preferably at least 1.7:1 and also yet more preferably at least 1.8:1. Too low a molar ratio for alkyl donor to gallium risks an incomplete reaction and a reduced yield of $RGaCl_2$ or $R_2GaCl/RGaCl_2$ mixture. But the molar ratio should be at most 5:1, more preferably at most 4.5:1 and yet more preferably at most 4:1. Too high a molar ratio for alkyl donor to gallium risks the process becoming too expensive overall. Particularly good yields of $RGaCl_2$ or $R_2GaCl/RGaCl_2$ mixture were obtained at between 1.8:1 and 3.8:1, in particular between 1.9:1 and 3.7:1, for the molar ratio of alkyl donor to gallium.

The invention provides that an activator is added for the reaction between gallium and the alkyl donor. This ensures high yields and a high purity of $RGaCl_2$ or $R_2GaCl/RGaCl_2$ mixture. The activator in the present invention is a gallium component, i.e. a compound comprising at least one gallium atom. However, for the purposes of the present invention, the term "gallium component" does not encompass elemental gallium. The gallium component as well as the gallium atom preferably comprises at least one alkyl group, at least one chlorine atom, or both. It is believed that the activators of the present invention are capable of contributing to the formation of reactive gallium(I) species which in turn are capable of adding the alkyl donor onto RGaCl$_2$ or R$_2$GaCl by oxidative addition reaction.

The activator of the present invention is preferably a compound or mixture of compounds having the following general formula:

$$R_aGa_bCl_c,$$

where a is selected from 0, 1, 2 and 3, b is selected from 1 and 2, and c is selected from 0, 1, 2 and 3 subject to the proviso that a and c are not both 0 and a+b+c is =4 or a multiple of 4, more preferably the sum total of a, b and c is =4 or 8, and where R is as defined above and where the sum total of a and c is 3 when b is 1, or where the sum total of a and c is 6 when b is 2.

It is very particularly preferable for the activator to be selected from gallium trichloride (GaCl$_3$), dialkylgallium chloride (R$_2$GaCl), R$_3$Ga$_2$Cl$_3$, RGaCl$_2$, and mixtures thereof. Such activators according to the present invention have proved to be particularly advantageous. It is very particularly preferable for the activator to be the reaction product.

It will be apparent to a person skilled in the art that it is also possible to use other halides including gallium trihalide, alkylgallium sesquihalide, dialkylgallium halide, alkylgallium dihalide and mixtures thereof, wherein the halide is selected from F, Br and I. However, it is particularly preferably for the halide to be chloride.

In one particularly preferred embodiment, the activator is R$_3$Ga$_2$Cl$_3$. R$_3$Ga$_2$Cl$_3$ is formable in situ, more preferably by preparing a mixture of GaCl$_3$ and R$_3$Ga. Such embodiments utilize a mixture of GaCl$_3$ and R$_3$Ga as activator precursor to form R$_3$Ga$_2$Cl$_3$ in situ. The molar ratio of GaCl$_3$ to R$_3$Ga in embodiments where the activator is R$_3$Ga$_2$Cl$_3$ or a mixture of GaCl$_3$ and R$_3$Ga is preferably between 0.5:1 and 1.5:1, more preferably between 0.7:1 and 1.3:1 and yet more preferably between 0.8:1 and 1.2:1. Such a molar ratio has been found to be particularly advantageous.

In alternative embodiments, the activator is the reaction product RGaCl$_2$ or R$_2$GaCl/RGaCl$_2$ mixture. This offers the additional advantage that a reaction vessel used for the reaction of the present invention is reusable because it still contains residues of compound (A), RGaCl$_2$ or an R$_2$GaCl/RGaCl$_2$ mixture which were not isolated and already act as an activator. One advantage of this procedure is a semi-continuous operation wherein only some of the reaction product is removed from the reactor and the reaction for preparing compound (A) can be continued after fresh gallium has been added. As a result, the process of the present invention can be made even more cost-effective.

In a further alternative embodiment, the activator is GaCl$_3$ or a mixture of GaCl$_3$ and RGaCl$_2$.

The molar ratio of gallium to activator is preferably more than 1:1, more preferably at least 1.1:1 and yet more preferably at least 1.2:1. A lower ratio of <1:1 makes the process too costly and inefficient. The molar ratio of gallium to activator is preferably of at most 50:1, more preferably at most 20:1 and yet more preferably at most 15:1. Using too little activator risks significant prolongation of the reaction, as a result of which the process can no longer be operated efficiently. In very particularly preferred embodiments, the molar ratio of gallium to activator is between 1.3:1 and 12:1 and more preferably between 2:1 and 10:1.

The weight ratios of gallium to activator, compound (A), are preferably in the range from about 1:5 to 12:1.

To prepare the reactant mixture, i.e., for the purposes of the present invention, the mixture comprising gallium, alkyl donor and activator, the individual components are added to a reaction vessel. Gallium and the alkyl donor are preferably added to the reaction vessel at separate times, i.e. in succession. It is particularly preferred to initially charge the reaction vessel with a pre-mix comprising gallium and activator and then to add the alkyl donor. This surprisingly leads to high yields and also simplified the apparatus requirements.

To wit, gallium and activator can simply be weighed into the reactor. This may be followed by a policed admixture of the alkyl donor which under DIN 1343:1990 standard conditions, is generally in the gaseous state. The alkyl donor, which under standard conditions is generally in the gaseous state (the boiling point is −24° C. in the case of MeCl and 12° C. in the case of EtCl), is preferably admixed into the reaction by policed continuous introduction in the liquid or gaseous state. The alkyl donor is in gaseous form in the reactor and/or under reaction conditions.

The alkyl donor is preferably introduced during the course of the reaction at a rate just equal to its rate of consumption, maintaining a constant reaction (over)pressure. A pressure sensor coupled to a metering valve is one example of effecting automatic control.

The alkyl donor preferably passes into the reactor in the liquid state. In general, the entire amount of alkyl donor needed is not admixed from the start, but instead alkyl donor is metered in on a permanent basis until the conversion is complete.

The liquid alkyl donor may be added, for example, directly under pressure from a liquid gas tank. Once in the reactor, the prevailing reaction conditions cause the alkyl donor to vaporize at once, so the reaction in the reactor is with gaseous alkyl donor.

In another embodiment, the alkyl donor, for example methyl chloride, passes in gaseous form into the reactor at room temperature and then is heated to the desired reaction temperature while the introduction of alkyl donor is continued throughout.

The reaction may be carried out under an inert gas such as argon or nitrogen, but it is also possible to carry out the reaction without additional inert gas, in a pure atmosphere of alkyl donor, for example methyl chloride or ethyl chloride, and this has advantages.

In general, the alkyl donor is admixed at a predetermined constant pressure, for example at an absolute pressure of 1.1 bar to 10 bar, or 1.5 bar to 6 bar or 2 bar to 4.5 bar (overpressure of 1 bar to 3.5 bar).

In one possible procedure, a desired overpressure of alkyl donor (that is, for example, ethyl chloride or methyl chloride), for example 3.5 bar, is predetermined. A flow rate controller is used to at all times add sufficient alkyl donor (that is, for example, ethyl chloride or methyl chloride) to the reactor as is consumed, so the pressure in the reactor remains approximately constant, for example at 4.5 bar (or at an overpressure of 3.5 bar). When the consumption of alkyl donor (that is, for example, ethyl chloride or methyl chloride) ceases, the reaction has ended.

Since the reaction may give rise to gaseous by-products such as ethene or methane, a tried and tested procedure is to occasionally relieve the overpressure in the reactor and recharge the reactor with alkyl donor. This may be advantageous in particular when, despite the presence of the starting materials, no consumption of alkyl donor can be observed even through this is inevitable when there is any reaction with the alkyl donor.

In another embodiment, the required amount of alkyl donor is fully charged to the reaction vessel right at the start of the reaction. In this embodiment, the alkyl donor is preferably admixed by condensing the alkyl donor into the reaction vessel. Preferably, in this embodiment, the pre-mix is initially cooled down after it has been prepared. It has been found to be advantageous to cool down the pre-mix to temperatures of at most 10° C., preferably at most 5° C. and more preferably below 4° C. It is very particularly advantageous for the pre-mix to be cooled down to a temperature of 0° C.+/−3° C.

Preferably, the reaction vessel is evacuated after the pre-mix has been cooled down. It is preferably at this stage that the alkyl donor is mixed at temperatures between −100° C. and −260° C., more preferably between −150° C. and −250° C. and yet more preferably at temperatures between −180° C. and −220° C. The step of admixing the alkyl donor preferably comprises condensing the alkyl donor into the reaction vessel, more preferably admixing the alkyl donor by condensing the alkyl donor into the reaction vessel. Such a procedure has been found advantageous to feed a defined amount of alkyl donor to the pre-mix in a technically simple manner. Under the process conditions which are preferred according to the present invention, the alkyl donor, which is generally gaseous under standard conditions, liquefies and in this state is easy to weight into the reaction vessel.

After the alkyl donor has been admixed, the reactant mixture is preferably heated in order start the reaction. Said heating may include some preliminary warming to temperatures between 15° C. and 35° C., preferably to room temperature, i.e. 25+/−5° C. The reactant mixture, preferably after said preliminary warming, is heated to temperatures of at least 100° C., more preferably at least 120° C. The temperature should not be too low or very long reaction times would be needed to achieve an adequate yield.

The process would then be less cost-effective. However, temperatures of preferably 300° C., more preferably 230° C. and even more preferably 200° C. should not be exceeded on heating. The process would then be too costly and risk unwanted secondary reactions.

The formation of compound (A) is exothermic and so, after heating the reactant mixture to at least 100° C., further heating of the reaction vessel is preferably not required, instead a constant reaction temperature is maintained. The reaction vessel is preferably maintained at a constant reaction temperature by cooling.

It has emerged to be particularly advantageous for a high yield and a high purity of compound (A), $RGaCl_2$, or a mixture of $R_2GaCl/RGaCl_2$, to maintain the reaction temperature at between 120° C. and 190° C., in particular at between 140° C. to 180° C., or at 130° C. and 170° C. and also, most preferably, at temperatures of 140° C. to 160° C., or of about 150+/−5° C.

In embodiments where the alkyl donor is completely added right at the start of the reaction, the pressure in the reaction vessel after heating may be at least 0.5 bar, or preferably at least 1 bar and most preferably at least 4 bar. An excessively low pressure leads to long reaction times making the process cost-intensive overall. It has proved to be particularly preferable for the pressure in the reaction vessel after heating to be between 1 to 15 bar, more preferably from 1 to 12 bar and even more preferably between 1 and 6 bar or 2 to 5 bar.

When the alkyl donor is added in a continuous manner, target pressures between 1.1 to 10 bar (absolute), preferably 1.5 to 6 bar, yet more preferably 2 to 4.5 bar (absolute, corresponding to an overpressure of 1 to 3.5 bar) can be used with success. At the reaction temperatures, the alkyl donor is usually gaseous at these pressures.

The reaction temperatures are preferably maintained for at least 20 min, more preferably for at least 30 min and yet more preferably for at least 40 min. Maintaining these temperatures for an excessively short time risks a non-quantitative reaction. According to the present invention, however, it is preferably not necessary to maintain the temperatures for more than 50 hours. In fact, owing in particular to the process management of the present invention and the reactant mixture composition of the present invention, adequate conversion is preferably achieved within 50 hours, preferably 28 hours and more preferably within 25 hours. Good results are usually obtainable with 6 to 12 hours, in particular 6 to 8 hours. This is advantageous because, as a result, the process of the present invention can be carried out in a particularly cost-effective manner.

In embodiments where the activator is $GaCl_3$ or a mixture of $GaCl_3$ and $RGaCl_2$, adequate yields of compound (A) were even obtainable on maintaining the temperatures—preferably obtained by heating—for a minimum of 45 min, preferably for a minimum of 50 min.

After the reaction temperatures have been maintained for the above-recited preferred period, or once there is no longer any metallic Ga, or there is no longer any consumption of alkyl donor, the mixture in the reaction vessel—hereinafter referred to as reaction mixture—is cooled down to temperatures between 15° C. and 35° C., preferably to room temperature, i.e. 25+/−5° C. In another embodiment, the alkyl donor feed is interrupted and the product is directly, without cooling, removed from the reactor in liquid form by discharging it from the reactor or pumping it into another vessel.

Reaction Step a2):

The optional isolation of compound (A), $RGaCl_2$ or $R_2GaCl/RGaCl_2$ mixture, referred to as reaction step a2) for the purposes of the present invention, preferably comprises separating any unconverted reactants from the reaction mixture and/or removing $RGaCl_2$ or $R_2GaCl/RGaCl_2$ mixture from the reaction vessel. This can be accomplished, for example, by mechanically removing $RGaCl_2$ or $R_2GaCl/RGaCl_2$ mixture or subliming $RGaCl_2$ or $R_2GaCl/RGaCl_2$ mixture from the reaction vessel.

Unconverted reactants are preferably removed from the reaction mixture, in particular the alkyl donor which is generally in gaseous form under standard conditions, by evacuating the reaction vessel, optionally at temperatures between 5° C. and 5° C., more preferably at 0+/−3° C. or room temperature.

The $RGaCl_2$ or $R_2GaCl/RGaCl_2$ mixture is mechanically removable from the reaction vessel after unconverted reactants have been removed from the reaction mixture. Mechanical removal also comprehends discharging or transfer pumping the reaction product in the liquid state. Alternatively, $RGaCl_2$ or $R_2GaCl/RGaCl_2$ mixture is sublimable from the reaction vessel. While mechanical removal is advantageous in relation to comparatively small batch sizes, sublimation has the advantage on the industrial scale that it is possible to operate a completely closed system where there is no longer any need for intervention from the outside.

Isolation may be followed by further steps to purify the $RGaCl_2$ or the $R_2GaCl/RGaCl_2$ mixture, in which case a person skilled in the art knows suitable processes for purifying chemical entities, for example sublimation or recrystallization, which can be accomplished very successfully from apolar compounds such as hydrocarbons. Aromatic or aliphatic hydrocarbons can both be used in principle, either individually or as mixture. Suitable entities for recrystallization include, for example, benzene, toluene, hexane, heptane, octane, spirits, petroleum ether or the like. Preferably, however, no further steps to purify the RGaCl$_2$ or R$_2$GaCl/RGaCl$_2$ mixture are required to achieve an adequate purity. Thus, according to the present invention, apart from separating unconverted reactants from the reaction mixture and preferably the subsequent mechanical removal of RGaCl$_2$ or R$_2$GaCl/RGaCl$_2$ mixture from the reaction vessel or its sublimation no further isolating and/or purifying steps are carried out.

In alternative embodiments, the RGaCl$_2$ or R$_2$GaCl/RGaCl$_2$ mixture is not isolated, i.e. step a) in these embodiments does not include a reaction step a2). In such embodiments, step b) can follow directly in the same reaction vessel without prior isolation of the RGaCl$_2$ or R$_2$GaCl/RGaCl$_2$ mixture. Such a form of process management can help to make the preparation of trialkylgallium compound altogether even more cost-effective and faster while maintaining high purity for the trialkylgallium compound obtained.

The present invention does not require the use of hydrogen (H$_2$) as a reaction accelerant during process step a1). The present invention similarly makes it possible to eschew the use of iodine or bromine or gallium triiodide or gallium tribromide, which in prior art processes typically had to be added to ensure complete conversion of gallium into galliumalkyl halide compounds. The latter is particularly advantageous with regard to the purity of RGaCl$_2$ or R$_2$GaCl/RGaCl$_2$ mixture.

Process step a1) of the present invention provides high yields of RGaCl$_2$ or R$_2$GaCl/RGaCl$_2$ mixture in the absence of organic solvents. Thus, the reaction of gallium with the alkyl donor in the presence of an activator to form RGaCl$_2$ or R$_2$GaCl/RGaCl$_2$ mixture preferably does not utilize an organic solvent. An organic solvent is defined by the present invention to be a carbonaceous liquid substance. By saying in the absence of an organic solvent the present invention means that no organic solvent is additionally used as reaction medium. This has the advantage that possible organic impurities in the RGaCl$_2$ or R$_2$GaCl/RGaCl$_2$ mixture due to partial decomposition of the solvent are avoided. In addition, the process can be carried out in an environmentally more benign manner as a result. Moreover, the absence of organic solvent in step a1) surprisingly coincided with a particularly high selectivity for the reaction.

Process step a) according to the present invention makes it possible to prepare RGaCl$_2$ or R$_2$GaCl/RGaCl$_2$ mixture in a yield of preferably at least 70%, more preferably at least 75%, yet more preferably at least 79%, yet still more preferably 85% and yet still even more preferably above 90% and most preferably of more than 95%. The yield particulars according to the invention are always based on the theoretical yield.

The purity of the RGaCl$_2$ or R$_2$GaCl/RGaCl$_2$ mixture obtained according to the present invention is preferably at least 95%, more preferably at least 98% and yet more preferably more than 99%. It is thus the case that preferably not more than 5%, more preferably not more than 2% and yet more preferably below 1% of impurities, i.e. undesired substances, are present in the RGaCl$_2$ or R$_2$GaCl/RGaCl$_2$ mixture obtained. A person skilled in the art is very familiar with methods for determining the purity of a chemical compound.

In one particularly preferred embodiment of the process according to the present invention, the following reaction takes place schematically in reaction step a) (Me=methyl):

In an alternative embodiment of the process according to the present invention the following reaction takes place schematically in reaction step a):

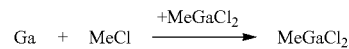

In a further alternative embodiment of the process according to the present invention, the following reaction takes place schematically in reaction step a):

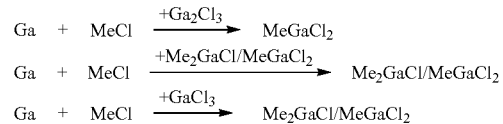

The RGaCl$_2$ or R$_2$GaCl/RGaCl$_2$ mixture obtained according to the present invention is useful for preparing trialkylgallium compound, i.e. step b) can follow directly or later, making it possible to prepare trialkylgallium compound in a specific manner and as and when needed.

b) Preparation of Trialkylgallium Compound from Alkylgallium Dichloride or R$_2$GaCl/RGaCl$_2$ Mixture Trialkylgallium compound is prepared from RGaCl$_2$ or R$_2$GaCl/RGaCl$_2$ mixtures in the manner of the present invention by reaction of RGaCl$_2$ or R$_2$GaCl/RGaCl$_2$ mixture with a metal alkyl component.

The metal alkyl component in the present invention is a compound comprising at least a metal atom and an alkyl group. The metal alkyl component preferably has the following general formula:

$$R_d M_e X_f$$

where d is selected from 1, 2 and 3 and e is selected from 1 and 2 and f is selected from 0, 1, 2 and 3 subject to the proviso that d and f are not both 0. R is as defined above. M is selected from aluminium, lithium and magnesium, and is particularly preferably aluminium or lithium. X is selected from Cl, Br and I, and preferably is Cl.

In preferred embodiments, M is aluminium, e is 1 or 2 and the sum total of d, e and f is =4 or 8, subject to the proviso that d is ≠0 and X is Cl, referred to as "aluminium alkyl component" for the purposes of the present invention. In alternative embodiments, M is magnesium, d is 1, e is 1, f is 1 and X is Cl, referred to as "magnesium alkyl component" for the purposes of the present invention. In further alternative embodiments, M is lithium, d is 1, e is 1 and f is 0, which is referred to as "lithium alkyl component" for the purposes of the present invention.

It is very particularly preferable for the metal alkyl component to be selected from RMgCl, R$_2$AlCl, R$_3$Al, R$_3$Al$_2$Cl$_3$ and RLi, more preferably selected from R$_2$AlCl, R$_3$Al, R$_3$Al$_2$Cl$_3$ and even more preferably selected from R$_3$Al and R$_3$Al$_2$Cl$_3$, especially Me$_3$Al, Et$_3$Al, Me$_3$Al$_2$Cl$_3$ and Et$_3$Al$_2$Cl$_3$.

The particular amount of metal alkyl component required relative to RGaCl$_2$ or R$_2$GaCl/RGaCl$_2$ mixture is determined by the number of alkyl groups in the metal alkyl component. When R$_2$GaCl/RGaCl$_2$ mixture is used for preparing R$_3$Ga, the amount of metal alkyl component is additionally determined by the ratio of R$_2$GaCl to RGaCl$_2$ in the mixture, i.e. by the number of alkyl groups in the mixture. The metal alkyl component is thus in each case used in an amount such that trialkylgallium compound can be formed quantitatively. In embodiments where the metal alkyl component is an aluminium alkyl component, the molar ratio of the metal alkyl component to RGaCl$_2$ can be between 0.7:1 to 4:1, preferably between 0.9:1 and 3.5:1, more preferably between 1:1 and 2:1. When a 50/50 mixture of R$_2$GaCl/RGaCl$_2$ mixture is used, for example, the molar ratio of the aluminium alkyl component to the R$_2$GaCl/RGaCl$_2$ mixture can be between 1:1 to 6:1. In the case of other compositions of the R$_2$GaCl/RGaCl$_2$ mixture, the ratios needed are easy to compute. Embodiments where the metal alkyl component is a "magnesium alkyl component" or a "lithium alkyl component", the molar ratio of the metal alkyl component to RGaCl$_2$ is typically between 1.9:1 to 4:1, preferably between 2:1 and 2.8. When a 50/50 R$_2$GaCl/RGaCl$_2$ mixture is used, for example, the molar ratio can be between 2.9:1 and 6:1, preferably 2:1 to 3:1.

The reaction of metal alkyl component with RGaCl$_2$ or R$_2$GaCl/RGaCl$_2$ mixture can take place in an organic solvent. Suitable organic solvents for step b) are selected from alkanes including cyclic saturated hydrocarbons, cyclic and aliphatic ethers and aromatic hydrocarbons with or without heteroatoms and/or substituents. Suitable organic solvents for step b) have been found to be in particular alkanes, aromatics and cyclic and aliphatic ethers, preferably selected from n-pentane, cyclohexane, cycloheptane, n-decane, n-heptane, n-hexane, n-nonane, n-octane and benzene, toluene, xylene, diethyl ether, comparatively long-chain ethers, tetrahydrofuran and mixtures thereof. Comparatively long-chain ethers are ethers having alkyl groups with more than 2 carbon atoms, particular preference being given to the comparatively long-chain ether di-n-butyl ether.

In preferred embodiments, however, no organic solvent is used in reaction step b), i.e. no organic solvent is additionally used as reaction medium. This has the advantage that possible organic impurities in the trialkylgallium compound due to partial decomposition of the solvent which appreciably limit the utility for MOCVD or MOVPE processes are avoided. In addition, the process can be carried out in an environmentally more benign manner as a result. In one embodiment according to the present invention, therefore, step b) is carried out in the absence of organic solvents.

An auxiliary base may further be added in reaction step b) because this can have a positive influence on the yield of trialkylgallium compound. Suitable auxiliary bases in step b) are selected from sodium chloride, potassium chloride, aluminium chloride and mixtures thereof. Very particular preference is given to a mixture of sodium chloride and potassium chloride, the molar ratio of sodium chloride to potassium chloride in the auxiliary base is preferably between 6:4 and 8:2, more preferably between 6:3 and 8:3 and yet more preferably between 6.5:3 and 7.5:3. In alternative embodiments where the auxiliary base is a mixture of aluminium chloride, sodium chloride and potassium chloride, the molar ratio of aluminium chloride to sodium chloride to potassium chloride is preferably 45 to 55:30 to 40:10 to 20, more preferably 50:35:15.

Preferably, RGaCl$_2$ or R$_2$GaCl/RGaCl$_2$ mixture is initially charged to the reaction vessel together with the optional auxiliary base and only thereafter the metal alkyl component is added, preferably gradually. The temperature at which the reaction takes place is chosen according to the metal alkyl component. The reaction preferably takes place at temperatures between 0° C. and 250° C., more preferably at 20° C. and 180° C. and yet more preferably at temperatures between 30° C. and 150° C. In embodiments where an auxiliary base is used, the temperature is preferably up to 230° C., more preferably up to 200° C. The temperature in such embodiments, however, is preferably at least 30° C.

The trialkylgallium compound is thereafter isolated from the remaining mixture in a step which may comprise removing optional organic solvents and also other constituents of the mixture. The trialkylgallium compound is preferably isolated from the mixture by distillative removal. In embodiments where an auxiliary base is added, the trialkylgallium compound is preferably isolated via a heatable separating element, in particular a heatable column. A heatable separating element such as a tube may serve for this in the simplest case, but also, for example, Vigreux columns, packed columns or other columns. Separating elements of this type are also known as separators, as is known from WO 2013/83450, the content of which is hereby incorporated in this application by reference. Further purifying steps may optionally follow in accordance with methods of purification known to a person skilled in the art, in particular a distillative removal or a sublimation of the trialkylgallium compound.

Process step b) of the present invention makes possible the preparation of trialkylgallium compound in a yield of preferably at least 70%, more preferably at least 70%, yet more preferably at least 75% and yet still more preferably at least 85% and also yet still more preferably above 90%. The purity of the trialkylgallium obtained according to the present invention is preferably at least 99%, more preferably at least 99.5% and yet more preferably more than 99.8% and also yet still more preferably more than 99.999%. The trialkylgallium obtained contains oxygen including gallium alkoxides and oxides in an amount of preferably below 100 ppm (m/m), preferably below 50 ppm (m/m) and yet more preferably below 30 ppm (m/m) and most preferably below 10 ppm (m/m). The oxygen content of trialkylgallium, or the level of oxygen-containing impurities in the trialkylgallium, can be determined using methods known to a person skilled in the art, in particular NMR.

In one particularly preferred embodiment of the process according to the invention, the following reaction proceeds in schematic form in reaction step b):

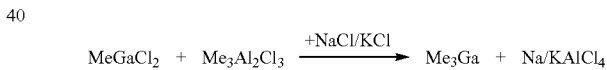

or when an R$_2$GaCl/RGaCl$_2$ mixture is used:

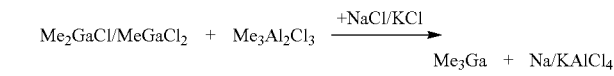

In one alternative embodiment of the process according to the present invention, the following reaction proceeds schematically in reaction step b):

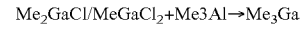

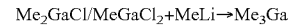

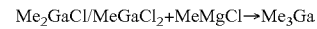

Trialkylgallium compound is obtainable in high purity and in high yield by complying with the conditions of the above-described preparation process of the present invention. The invention additionally provides the alkylgallium dichloride obtained by the process, or the dialkylgallium chloride/alkylgallium dichloride mixture, in particular methylgallium dichloride or $Me_2GaCl/MeGaCl_2$, as intermediate stage, and the trialkylgallium compound, in particular trimethylgallium prepared therefrom. When lithium species or Grignard species are used as metal alkyl component, e.g. methyllithium or methylmagnesium chloride, good results are obtainable by performing the reaction in a solvent. Solvents of high suitability include, for example, ethers, such as diethyl ether, di-n-butyl ether, methyl tert-butyl ether, ethyl tert-butyl ether, dioxane or tetrahydrofuran.

Especially the possible high yield and purity of $RGaCl_2$ or $R_2GaCl/RGaCl_2$ mixture and $R_3Ga$ and also the cost-efficient and environmentally minimally impactful choice of processes within the process of the present invention, virtually predestines said process for industrial preparation of trialkylgallium compounds.

The process of the present invention is characterized in particular by a particularly high gallium efficiency. The overall gallium conversion in the process according to the present invention, based on the gallium used, is preferably ≥70%, more preferably ≥75%, still more preferably ≥80% and yet still more preferably >95%.

The trialkylgallium compound, in particular trimethylgallium, obtainable with the process of the present invention is by virtue of its outstanding purity, in particular the very low oxygen content, particularly useful as organometallic precursor for MOCVD or MOVPE, for example for production of semiconductors or semiconductor components. The ultimately produced semiconductors or semiconductor components have many possible industrial uses. The invention therefore also provides for the use of the trialkylgallium compound, preferably trimethylgallium, obtained according to the present invention as a precursor for metal-organic chemical vapour deposition (MOCVD) or metal-organic vapour phase epitaxy (MOVPE).

Working Examples of Preparing Trimethylgallium

Trimethylgallium was prepared by the inventive process via the intermediate stage of methylgallium dichloride.

1. Preparation of Methylgallium Dichloride 1.1. Reaction of Gallium with Methyl Chloride in the Presence of $Me_3Ga_2Cl_3$ as Activator (Formed In Situ, Molar Ratio of Gallium to Activator: About 8.8:1)

1.17 g of gallium (16.8 mmol), 0.21 g of $Me_3Ga$ (1.9 mmol) and 0.32 g of $GaCl_3$ (1.8 mmol) were weighed into a 250 ml Parr bomb together with a magnetic stirbar. The vessel was cooled to 0° C. and evacuated. Then, 3.06 g of methyl chloride (60.7 mmol) were condensed into the Parr bomb at −196° C. and, after warming to room temperature, the Parr bomb was heated to 160° C. After 24 hours at 160° C. the gallium had completely dissolved, the Parr bomb was then cooled down to room temperature and, on reaching room temperature, the Parr bomb was evacuated at 0° C. in order to remove residues of methyl chloride and to determine the increase in mass. The Parr bomb was subsequently opened in a glove box and the $MeGaCl_2$ was mechanically isolated. The $MeGaCl_2$ yield as per the mass increase was 3.18 g (20.4 mmol, 99%). Of that, 2.57 g (16.5 mmol, 80%) were mechanically isolated. Identification was by NMR and IR.

1.2. Reaction of Gallium with Methyl Chloride in the Presence of $MeGaCl_2$ (Molar Ratio of Gallium to Activator: About 1.7:1)

1.14 g of gallium (16.4 mmol) and 1.46 g of $MeGaCl_2$ (9.4 mmol) were weighed into a 250 ml Parr bomb together with a magnetic stirbar. The vessel was cooled to 0° C. and evacuated. Then, 2.99 g of methyl chloride (59.2 mmol) were condensed into the Parr bomb at −196° C. and, after warming to room temperature, the Parr bomb was heated to 160° C. After 21 hours at 160° C. the gallium had completely dissolved, the Parr bomb was then cooled down to room temperature and, on reaching room temperature, the Parr bomb was evacuated at 0° C. in order to remove residues of methyl chloride and to determine the increase in mass. The Parr bomb was subsequently opened in a glove box and the $MeGaCl_2$ was isolated. The $MeGaCl_2$ yield as per the mass increase was 4.03 g (25.9 mmol, 99%). Of that, 3.87 g (24.9 mmol, 96%) were mechanically isolated. Identification was by NMR and IR.

1.3. Reaction of Gallium with Methyl Chloride in the Presence of $GaCl_3$ (Molar Ratio of Gallium to $GaCl_3$: 2:1)

0.70 g of gallium (10.0 mmol) and 0.89 g of $GaCl_3$ (5.0 mmol) were weighed into a 125 ml Parr bomb together with a magnetic stirbar. The vessel was cooled to 0° C. and evacuated. Then, 1.03 g of methyl chloride (20.4 mmol) were condensed into the Parr bomb at −196° C. and, after warming to room temperature, the Parr bomb was heated to 160° C. After 90 min at 160° C. the gallium had completely dissolved, the Parr bomb was then cooled down to room temperature and, on reaching room temperature, the Parr bomb was evacuated at 0° C. in order to remove residues of methyl chloride and to determine the increase in mass. The Parr bomb was subsequently opened in a glove box and the $MeGaCl_2$ was isolated. Residues of $MeGaCl_2$ remained in the Parr bomb and could not be removed mechanically. The $MeGaCl_2$ yield as per the mass increase was 2.28 g (14.6 mmol, 98%). Of that, 1.94 g (12.5 mmol, 83%) were mechanically isolated. Identification was by NMR and IR.

1.4. Reaction of Gallium with Methyl Chloride in the Presence of $GaCl_3$ (Molar Ratio of Gallium to $GaCl_3$: 2:1, Additionally Residues of $MeGaCl_2$ in the Reaction Vessel)

The 125 ml Parr bomb from preceding Example 1.3 was used. Neither the Parr bomb nor the magnetic stirbar was cleaned. The residues of $MeGaCl_2$ remained in the Parr bomb. 0.70 g of gallium (10.0 mmol) and 0.89 g of $GaCl_3$ (5.0 mmol) were charged to the Parr bomb together with a magnetic stirbar. The vessel was cooled to 0° C. and evacuated. Then, 1.18 g of methyl chloride (23.4 mmol) were condensed into the Parr bomb at −196° C. and, after warming to room temperature, the vessel was heated to 160° C. During the reaction, the melt was dark in colour. After 60 min at 160° C., the Parr bomb was cooled down to room temperature and was then evacuated at 0° C. in order to remove residues of methyl chloride and to determine the increase in mass. The Parr bomb was subsequently opened in a glove box and the $MeGaCl_2$ was isolated. Residues of $MeGaCl_2$ remained in the Parr bomb and could not be removed mechanically. Compared with the preceding batch, the isolated $MeGaCl_2$ had a brown colour. The $MeGaCl_2$ yield as per the mass increase was 2.24 g (15.4 mmol, quantitative, based on Ga and $GaCl_3$ used). Of that, 2.54 g (16.3 mmol) were mechanically isolated. Identification was by NMR and IR.

The combined mass of $MeGaCl_2$ product from Examples 1.3 and 1.4 was 4.62 g of $MeGaCl_2$ (29.7 mmol, yield: 99%). The isolated yield for both runs together was 4.48 g $MeGaCl_2$ (28.8 mmol, 96%).

1.5 Reaction of Gallium with Methyl Chloride in the Presence of $Me_2GaCl/MeGaCl_2$ Mixture and Continuous Feeding of Alkyl Donor A 1 L pressure reactor was initially charged with 86.63 g (1.24 mol) of gallium. The reactor was inertized by threefold evacuation/flooding with argon, after the last evacuation chloromethane was used to bring the reactor back to atmospheric pressure instead of argon. A heated dropping funnel at 90° C. was used to drain 198.77 g of Me$_2$GaCl/MeGaCl$_2$ mixture (from a previous charge) into the reactor in liquid form. To initiate the reaction, the reaction mixture was heated to 150° C. under agitation before 5 bar of chloromethane (absolute, corresponds to 4 bar of overpressure) was injected into the reactor. The starting of the reaction was evident from the onset of gas absorption and from an exotherm. The MeCl feed into the reactor was controlled so as to maintain the reaction pressure at a constant 5 bar. The reaction temperature was maintained at 150° C. by cooling the reactor. After about four hours, the gas absorption of the reaction had dropped to below 100 mL/min even though there still was some gallium in the melt, which is why the overpressure of the reactor was released, then a further 5 bar of MeCl were injected and the reaction was continued. After a further half an hour, gallium was no longer visible in the reactor and the reaction no longer consumed gas. The gas feed was stopped and the reaction mixture was cooled down to room temperature. The overpressure remaining in the reactor was released and then the reactor was evacuated to remove the residual chloromethane and volatile byproducts and brought back to standard pressure with argon.

To isolate the product, the reactor was heated to 70° C., as a result of which the reaction product melted and the melt was distilled out of the reactor at 80-100° C. under reduced pressure. This gave 377.42 g of a white crystalline solid. The 1H NMR (600 MHz, CD3CN) showed two singlets at −0.09 ppm and 0.14 ppm in a ratio of 0.39:1, which were assigned to a (CH$_3$)$_2$GaCl unit and a (CH$_3$)GaCl$_2$ unit. This corresponds to a molar Me2GaCl/MeGaCl2 ratio of about 28/72. The gallium yield based on the metallic gallium used was 92.3%. The isolated product was 95.9% pure.

1.6 Reaction of Gallium with MeCl in the Presence of GaCl$_3$ and Continuous Feeding of Alkyl Donor An inert 1 L pressure reactor was initially charged with 105.2 g (1.51 mol) of gallium and 127.9 g (0.73 mol) of GaCl$_3$. The reactor was evacuated and injected with chloromethane. The reaction mixture was heated to 150° C. under agitation and at a target overpressure of 4.5 bara chloromethane was introduced at 150° C. into the reactor at a max. of 1000 mL/min for 1.5 hours until all the gallium had been consumed and chloromethane was no longer consumed. The overall consumption of chloromethane was 58 L. The overpressure in the reactor was released, the reactor was cooled down and about ⅓ of the reaction product was drained in liquid form from the reactor into a Schlenk flask. The remainder of the reaction product was cooled down to room temperature and remained as a solid in the reactor for use in a subsequent run.

163.3 g of Me$_2$GaCl/MeGaCl$_2$ mixture were isolated in the form of a crystalline white solid. $^1$H NMR (600 MHz, CD$_3$CN) δ −0.02 (s, (CH$_3$)$_2$Ga), 0.18 (s, CH$_3$Ga); integral ratio 1:9, which corresponds to a molar Me$_2$GaCl/MeGaCl$_2$ ratio of about 5/95.

1.7 Reaction of Gallium with MeCl in the Presence of Me$_2$GaCl/MeGaCl$_2$ Mixture and Continuous Feeding of Alkyl Donor The reactor containing the Me$_2$GaCl/MeGaCl$_2$ mixture from the previous example was charged with 101.6 g (1.46 mol) of gallium. The reaction mixture was then again heated to 150° C. under agitation and at a target overpressure of 4.5 bara chloromethane was introduced at 150° C. into the reactor at a max. of 1000 mL/min for 2 hours until all the gallium had been consumed and chloromethane was no longer consumed. The overall consumption of chloromethane was 55.5 L. The overpressure in the reactor was released, the reactor was cooled down and at 100° C. about ⅓ of the reaction product was drained in liquid form from the reactor into a Schlenk flask. The remainder of the reaction product was cooled down to room temperature and remained as a solid in the reactor for use in a subsequent run. The isolated product was purified by sublimation under reduced pressure.

169.6 g of Me$_2$GaCl/MeGaCl$_2$ mixture were isolated in the form of a crystalline white solid. $^1$H NMR (600 MHz, C$_6$D$_6$) δ 0.17 (s, (CH$_3$)$_2$Ga), 0.28 (s, CH$_3$Ga); integral ratio 1:1.49, which corresponds to a molar Me$_2$GaCl/MeGaCl$_2$ ratio of about 25/75; Ga content: 47.4%.

1.8 Reaction of Gallium with MeCl in the Presence of Me$_2$GaCl/MeGaCl$_2$ Mixture and Continuous Feeding of Alkyl Donor The reactor containing the Me$_2$GaCl/MeGaCl$_2$ mixture from the previous example was charged with 105.6 g (1.51 mol) of gallium. The reaction mixture was then again heated to 150° C. under agitation and at a target overpressure of 4.5 bara chloromethane was introduced at 150° C. into the reactor. After four hours gas consumption declined substantially, at which point the pressure in the reactor was released and fresh chloromethane was used to reestablish the target overpressure. Chloromethane was introduced for a further 1.5 hours until all the gallium had been consumed. The overall consumption of chloromethane was 55.5 L. The overpressure in the reactor was released, the reactor was cooled down and at 100° C. about ⅓ of the reaction product was drained in liquid form from the reactor into a Schlenk flask. The remainder of the reaction product was cooled down to room temperature and remained as a solid in the reactor for use in a subsequent run. The isolated product still contained small amounts of short-chain hydrocarbons as impurity and was purified by sublimation under reduced pressure.

192.2 g of Me$_2$GaCl/MeGaCl$_2$ mixture were isolated in the form of a crystalline white solid. $^1$H NMR (600 MHz, CD$_3$CN) δ −0.10 (s, (CH$_3$)$_2$Ga), 0.14 (s, CH$_3$Ga); integral ratio 1:1.13, which corresponds to a molar Me$_2$GaCl/MeGaCl$_2$ ratio of about 30/70.

$^1$H NMR (600 MHz, CD$_3$CN) δ-0.10 (s, 6H, (—Ga(CH$_3$)$_2$), 0.14 (s, 3H(—Ga(CH$_3$))

Preparation of Trimethylgallium 2.1 Conversion of Methylgallium Dichloride into Trimethylgallium A 500 mL flask equipped with a stirrer and a heated separator at 70° C. was initially charged under protective gas with 1.94 g (12.5 mmol) of MeGaCl$_2$ from Example 1.1, 1.2 or 1.3, 1.02 g (17.5 mmol) of dry NaCl and 0.56 g (7.5 mmol) of dry KCl. Under agitation 2.56 g (2.2 ml, 12.5 mmol) of Me$_3$Al$_2$Cl$_3$ were admixed such that the temperature in the reaction mixture did not rise above 130° C. During the subsequent heating-up, Me$_3$Ga was isolated at above about 150° C. in an amount of 1.25 g (10.9 mmol, 87.6% direct yield based on MeGaCl$_2$ used). The isolation of product via the separator was terminated as soon as the reaction temperature rose to above 200° C., thereafter remaining gallium-containing compounds were removed from the reaction mixture in a high vacuum via a second outlet (0.095 g, mixture of Me$_3$Ga and Me$_2$GaCl). Overall yield: 94.8% of Me$_3$Ga, 5.0% of Me$_2$GaCl, overall gallium conversion: 99.8%.

2.2 Reaction of Gallium with Methyl Chloride in the Presence of GaCl$_3$ (Molar Ratio of Gallium to GaCl$_3$: 2:1) with Subsequent Conversion into Trimethylgallium 1.39 g of gallium (19.9 mmol) and 1.76 g of GaCl$_3$ (10.0 mmol) were weighed into a 125 mL Parr bomb and, after evacuation, 1.87 g of methyl chloride (37.0 mmol) were condensed into the Parr bomb. The Parr bomb was heated at 160° C. for one hour. During this period, the gallium dissolved completely and a colourless melt was observed. After excess methyl chloride had been pumped off, a mass increase of 1.60 g was determined. This corresponds to a quantitative conversion of the Ga/GaCl$_3$ mixture into MeGaCl$_2$. Subsequently 1.63 g of NaCl (27.9 mmol), 0.89 g of KCl (11.9 mmol) and 4.06 g of methylaluminium sesquichloride (19.7 mmol) were weighed into the Parr bomb. The Parr bomb was heated to 130-140° C. overnight. After cooling to room temperature, the volatile constituents were condensed in a cold trap cooled to −196° C. under reduced pressure. During this, the Parr bomb was heated to 160° C. under reduced pressure. A mixture of Me$_2$GaCl and GaMe$_3$ was obtained in the cold trap. The more volatile GaMe$_3$ was condensed at atmospheric pressure into a further cold trap cooled to −196° C. 3.46 g of Me$_2$GaCl (25.6 mmol, 86%) and 0.18 g of GaMe$_3$ (1.6 mmol, 5%) were isolated.

The invention claimed is:

1. A process for preparing a compound (A), the formula

RGaCl$_2$ or a mixture of RGaCl$_2$ with R$_2$GaCl, comprising the reaction steps of
   a1) reacting gallium with a gaseous alkyl donor in the presence of an activator to form compound (A) at a pressure of 1.1 bar to 10 bar,
   a2) and optionally isolating said compound (A) from the reaction mixture,
   where R is branched or unbranched alkyl of 1 to 4 carbon atoms and
   wherein the activator is selected from the group consisting of R$_2$GaCl, R$_3$Ga$_2$Cl$_3$, RGaCl$_2$ and mixtures thereof, or is a mixture of R$_2$GaCl and RGaCl$_2$, or wherein the reaction product, compound (A), is itself used as activator.

2. The process according to claim 1, wherein the alkyl donor has the general formula:

RCl where R is as defined above.

3. The process according to claim 1, wherein R is methyl.

4. The process according to claim 1, wherein R is ethyl.

5. The process according to claim 1, wherein the molar ratio of alkyl donor to gallium is at least 1.4:1.

6. The process according to claim 1, wherein a premix of gallium and activator is initially charged to the reaction vessel in reaction step a1) and the alkyl donor is added subsequently.

7. The process according to claim 1, wherein reaction step a1) is carried out in the absence of organic solvents.

8. A process for preparing a compound (B) of the general formula:

R$_3$Ga which process comprises providing a compound (A) of the formula

RGaCl$_2$ or a mixture of RGaCl$_2$ with R$_2$GaCl, comprising the reaction steps of
   a1) reacting gallium with a gaseous alkyl donor in the presence of an activator to form compound (A), wherein the activator is selected from R$_2$GaCl, R$_3$Ga$_2$Cl$_3$, RGaCl$_2$ and mixtures thereof, or is a mixture of R$_2$GaCl and RGaCl$_2$, or wherein the reaction product, compound (A), is itself used as activator,
   a2) and optionally isolating said compound (A) from the reaction mixture,
   where R is branched or unbranched alkyl of 1 to 4 carbon atoms
   and
   b) reacting said compound (A) with a metal alkyl component to obtain a compound (B) of the general formula:

R$_3$Ga where R is defined above and wherein the metal alkyl component is RMgCl, R$_2$AlCl, R$_3$Al$_2$Cl$_3$ or RLi.

9. The process according to claim 8, wherein the metal alkyl component is R$_3$Al$_2$Cl$_3$.

10. The process according to claim 8, wherein the metal alkyl component is Me$_3$Al$_2$Cl$_3$ or Et$_3$Al$_2$Cl$_3$.

11. The process according to claim 8, wherein an auxiliary base is also added in reaction step b), wherein the auxiliary base is selected from the group consisting of sodium chloride, potassium chloride, aluminium chloride and mixtures thereof.

12. The process according to claim 1, wherein said compound (A) is a mixture of the compounds R$_2$GaCl and RGaCl$_2$, where R is as defined above, and the ratio of R$_2$GaCl to RGaCl$_2$ is in the range from 10:90 to 90:10 based on the molar amounts.

13. The process according to claim 1, wherein said compound (A) is a mixture of the compounds R$_2$GaCl and RGaCl$_2$, where R is as defined above, and the ratio of R$_2$GaCl to RGaCl$_2$ is in the range from 10:90 to 50:50 based on the molar amounts.

14. The process according to claim 1, wherein said compound (A) is a mixture of the compounds R$_2$GaCl and RGaCl$_2$, where R is as defined above, and the ratio of R$_2$GaCl to RGaCl$_2$ is in the range from 20:80 to 40:60 based on the molar amounts.

15. The process according to claim 10, wherein the metal alkyl component is Me$_3$Al$_2$Cl$_3$.

16. The process according to claim 10, wherein the metal alkyl component is Et$_3$Al$_2$Cl$_3$.

17. The process according to claim 1, wherein the gaseous alky donor is condensed in the reaction so that the alkyl donor is liquefied.

18. A process for preparing a compound (A), which is either of the general formula RGaCl$_2$ or is a mixture of RGaCl$_2$ with R$_2$GaCl, comprising the reaction steps of
   a1) reacting gallium with a gaseous alkyl donor in the presence of an activator to form compound (A), wherein the alkyl donor is introduced during the course of the reaction at a rate just equal to the consumption, maintaining a constant reaction pressure of 2 to 10 bar,
   a2) and optionally isolating said compound (A) from the reaction mixture, where R is branched or unbranched alkyl of 1 to 4 carbon atoms and
   wherein the activator is selected from R$_2$GaCl, R$_3$Ga$_2$Cl$_3$, RGaCl$_2$ and mixtures thereof, or is a mixture of R$_2$GaCl and RGaCl$_2$, or wherein the reaction product, compound (A), is itself used as activator.

19. The process according to claim 18, wherein the reaction pressure is from 2 to 6 bar.

20. The process of claim 1 wherein some of the reaction product is removed from the reactor and the reaction for preparing compound (A) is continued after fresh gallium has been added.

21. A process of preparing a compound (B) of the general formula $R_3Ga$, comprising
  comprising the reaction steps of
  a1) reacting gallium with a gaseous alkyl donor in the presence of an activator to form compound (A) at a pressure of 1.1 bar to 10 bar,
  a2) and optionally isolating said compound (A) from the reaction mixture,
    where R is branched or unbranched alkyl of 1 to 4 carbon atoms and
  wherein the activator is selected from the group consisting of $R_2GaCl$, $R_3Ga_2Cl_3$, $RGaCl_2$ and mixtures thereof, or is a mixture of $R_2GaCl$ and $RGaCl_2$, or wherein the reaction product, compound (A), is itself used as activator
and
b) reacting said compound (A) with a metal alkyl component to obtain a compound (B) of the general formula:

$R_3Ga$ where R is a branched or unbranched alkyl of 1 to 4 carbon atoms.

* * * * *